United States Patent [19]
Hall et al.

[11] Patent Number: 6,060,617
[45] Date of Patent: May 9, 2000

[54] CONTAMINANT FREE ORGANOMETALLIC AMIDE COMPOSITIONS AND PROCESSES FOR MAKING SAME

[75] Inventors: Randy W. Hall, Kings Mountain, N.C.; Bobby J. McElroy, York, S.C.; James A. Schwindeman, Lincolnton, N.C.; Conrad W. Kamienski, Gastonia, N.C.; Terry L. Rathman, Gastonia, N.C.; Robert C. Morrison, Gastonia, N.C.

[73] Assignee: FMC Corporation, Philadelphia, Pa.

[21] Appl. No.: 08/670,348

[22] Filed: Jun. 25, 1996

Related U.S. Application Data

[60] Provisional application No. 60/000,627, Jun. 30, 1995, provisional application No. 60/002,333, Aug. 15, 1995, and provisional application No. 60/002,336, Aug. 15, 1995.

[51] Int. Cl.[7] .................................................. C07F 7/10
[52] U.S. Cl. ............................................... 556/410
[58] Field of Search ............................................... 556/410

[56] References Cited

U.S. PATENT DOCUMENTS

| | | |
|---|---|---|
| 4,595,779 | 6/1986 | Morrison et al. . |
| 5,002,689 | 3/1991 | Mehta et al. . |
| 5,149,457 | 9/1992 | Smith . |
| 5,420,322 | 5/1995 | Chiu et al. . |

OTHER PUBLICATIONS

Zhurnal Obschei Khimii, vol. 58, No. 8, 1988, pp. 1934–1935, XP002012079, Magedov, I.V. et al.: "Convenient Method For The Preparation of (Bis(Trimethylsilyl)Amino)Lithium".

Chemical Abstracts, vol. 66, No. 7, Feb. 13, 1967, Columbus, Ohio, US; abstract No. 28834m, Krueger, C.R. et al.: "Sodium Bis(Trimethylsilyl) Amide and Tris (Trimethylsilyl) Amine", XP002012081, see abstract & Inorg. Syn., vol. 9, 1966, pp. 15–19.

Russian Chemical Bulletin, vol. 44, No. 11, Nov., 1995, pp. 2197–2198, XP002012080, Magedov, I.V. et al.: "Convenient Method For The Preparation of Potassium Bis(Trimethylsilyl) Amide".

*Primary Examiner*—Paul F. Shaver
*Attorney, Agent, or Firm*—Alston & Bird LLP

[57] ABSTRACT

Organometallic amide compositions and processes for preparing the same, for example, by: reacting an alkali metal, alkali metal hydride, or alkali metal amide with a substituted amine in the absence of an electron carrier; reacting an alkali metal with a substituted amine in the presence of an electron carrier in a hydrocarbon solvent; distilling a composition which includes an alkali metal amide and a reduced electron carrier to recover the alkali metal amide; reacting an alkali metal with a substituted amine in the presence of an alkyl halide; and reacting a substituted amine capable of reacting with an alkali metal to form a hydrocarbon insoluble alkali metal amide with an alkali metal in the presence of a substituted amine capable of reacting with an alkali metal to form a hydrocarbon soluble alkali metal amide.

38 Claims, No Drawings

CONTAMINANT FREE ORGANOMETALLIC AMIDE COMPOSITIONS AND PROCESSES FOR MAKING SAME

CROSS-REFERENCE TO RELATED APPLICATIONS

This application is related to commonly owned copending Provisional Application Ser. No. 60/000,627, filed Jun. 30, 1995; Provisional Application Ser. No. 60/002,333, filed Aug. 15, 1995; and Provisional Application Ser. No. 60/002,336, filed Aug. 15, 1995, and claims the benefit of their earlier filing dates under 35 U.S.C. 119(e).

FIELD OF THE INVENTION

This invention relates to alkali metal amide compositions which are free of organic contaminants or byproducts and to processes for preparing the same.

BACKGROUND OF THE INVENTION

Highly substituted lithium amide bases can be expressed by the formula $(R_3M)_xNLi(R^1)_y$ where M=Si or C, R and $R^1$ are alkyl, cycloalkyl and alkylene groups containing 1 to 8 carbon atoms, and x+y=2. $R_3M$ and $R^1$ may be combined (where M=C) to give a divalent alkylene radical, yielding a lithium cyclic alkylene amide where R and $R^1$ taken together may contain 4 to 8 carbon atoms such as the N-lithio salts of pyrrolidine and hexamethyleneimine. Highly substituted or bulky lithium amide bases of this type are used in the preparation of pharmaceutical intermediates and in general organic synthesis.

U.S. Pat. Nos. 4,595,779 and 5,002,689 describe methods for producing highly substituted lithium amide bases in ether or mixed ether/hydrocarbon solvents using lithium metal in dispersed form and an electron carrier compound such as styrene or isoprene. U.S. Pat. No. 5,149,457 describes a method of producing highly substituted lithium amide bases in solely hydrocarbon solvent media by reacting alkyllithium compounds, such as n-butyllithium, with highly substituted amine bases, such as diisobutylamine.

While useful, these and other techniques can result in the formation of undesirable byproducts. For example, the processes described in U.S. Pat. Nos. 4,595,779 and 5,002,689 can result in the reduction products ethylbenzene and 2-methyl-2-butene of the electron carriers styrene and isoprene, respectively. The process described in U.S. Pat. No. 5,149,457 results in saturated alkanes as a byproduct, resulting from protonation of the alkyllithium compounds by the highly substituted amine bases.

The presence of these by-products in the desired product, highly substituted lithium amide base solutions, is often detrimental in subsequent applications, primarily because they can pose problems in recovery of final pure solvents from recycle streams. Additionally, the alkane by-products, such as butane, can pose environmental and safety concerns.

U.S. Pat. No. 5,420,322 describes a method for circumventing this problem of by-product impurities by directly reacting the highly substituted amine base, i.e., hexamethyldisilazane, with alkali metals above their melting points, in the absence of electron carriers. Thus the reaction temperature for lithium metal is 225° C. and the reactor must be made of steel (molten lithium metal attacks glass) to withstand the pressures required for use with most ordinary solvents, e.g., tetrahydrofuran and cyclohexane. The use of molten lithium metal at these reaction temperatures is hazardous, since inadvertent exposure to the ambient atmosphere would result in instant conflagration. In addition, the process is expensive with respect to energy expended and capital cost of the pressure equipment needed. Also, best results were obtained using an excess of the base, i.e., hexamethyldisilazane, thus necessitating the use of a second solvent to dissolve the reaction product after reaction was cooled to ambient temperature.

SUMMARY OF THE INVENTION

The present invention provides alkali metal amide compositions which are substantially free of organic contaminates, such as reduced electron carriers, saturated alkanes, and the like. The invention also provides processes for the production of contaminate-free alkali metal amide compositions. The processes of the invention do not require reaction temperatures above the melting point of lithium metal, thus providing economies of production. Further, the processes of the invention can be conducted under relatively mild reaction conditions in various solvents, including ethereal, hydrocarbon, and amine solvent systems, and mixtures thereof. Still further, the processes of the invention can be conducted in the absence of electron carriers or alkyllithium compounds. Alternatively, the processes of the invention can provide efficient and safe removal of reduced electron carriers and/or saturated alkanes when present, thus minimizing or eliminating the problems associated with the use of electron carriers and alkyl lithium compounds to prepare alkali metal amide compositions.

In one embodiment of the invention, organometallic amide compositions are prepared by reacting alkali metals, alkali metal hydrides, or alkali metal amides with a substituted amine in the absence of an electron carrier. The resultant alkali metal amide composition is substantially free of organic contaminants.

In another embodiment of the invention, an alkali metal is reacted with a substituted amine in the presence of an electron carrier in an inert hydrocarbon solvent. The resultant alkali metal amide is substantially insoluble in the hydrocarbon solvent and accordingly precipitates and can be readily recovered. Any reduced electron carrier adhering to the recovered alkali metal amide can be removed by washing the alkali metal amide with additional hydrocarbon solvent. The resultant alkali metal amide can thereafter be treated to provide a composition thereof.

In another embodiment of the invention, a composition comprising an alkali metal amide and byproducts, such as reduced electron carrier, is distilled to separate the alkali metal amide from the byproducts. The recovered alkali metal amide can then be treated, i.e., dissolved, in a suitable solvent to provide an alkali metal amide composition which is substantially free of organic contaminants.

Yet another embodiment of the invention includes reacting an alkali metal with a substituted amine in the presence of an alkyl halide. The resultant reaction mixture includes byproducts, such as alkane gases and alkali metal salts, which are insoluble in the solvent, and accordingly can be readily recovered to provide contaminate free alkali metal amide compositions.

In yet another embodiment of the invention, substituted amines capable of reacting with an alkali metal to form a hydrocarbon insoluble alkali metal amide are reacted with an alkali metal in an inert hydrocarbon solvent in the presence of a substituted amine capable of reacting with an alkali metal to form a hydrocarbon soluble alkali metal amide. The resultant insoluble alkali metal amide can be recovered from the reaction mixture and thereafter treated to provide a composition thereof.

DETAILED DESCRIPTION OF THE INVENTION

The present invention provides high purity alkali metal, i.e., lithium, potassium, and sodium, amide compositions which are substantially free of organic contaminants or by-products, as well as processes for preparing the same. The alkali metal amides can be generally represented by the formula $(R_3M)_xNT(R^1)_y$ wherein M=Si or C, R and $R^1$ are C1 to C8 alkyl, cycloalkyl and alkylene groups, x+y=2, and T is an alkali metal. $R_3M$ and $R^1$ may be combined (wherein M=C) to give a divalent alkylene radical, yielding an alkali metal cyclic alkylene amide wherein R and $R^1$ together contain 4 to 8 carbon atoms. Exemplary highly substituted lithium amide bases include, but are limited to, lithium diisopropylamide, lithium hexamethyleneimide, lithium diisobutylamide, lithium tert-butyl-methylamide, lithium tert-butyltrimethylsilylamide, lithium cyclohexylisopropylamide, lithium cyclohexylmethylamide, lithium allyl-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(S)-1-phenylethylamide, lithium bis-(1-phenylethyl)amide, lithium (+)-bis-[(R)-1-phenylethyl]amide, lithium (−)-bis-[(S)-1-phenylethyl]amide, lithium 2,2,6,6-tetramethylpiperidide, lithium pyrrolidide, lithium piperidide and lithium hexamethyldisilazide (LHS).

The compositions can further include ethereal or hydrocarbon solvents, or mixtures thereof (i.e., ethereal-hydrocarbon solvents). Examples of ethereal solvents useful in the invention include, but are not limited to, tetrahydrofuran (THF), 2-methyltetrahydrofuran, diethyl ether, t-butyl methyl ether, dibutyl ether, diethoxymethane, 1,2-dimethoxyethane (glyme), diglyme, triglyme, and mixtures thereof. Examples of liquid hydrocarbon solvents useful in the practice of this invention include, but are not limited to, hexane, cyclohexane, heptane, toluene, ethylbenzene, and xylene.

As the skilled artisan will appreciate, various highly substituted lithium amide bases, such as lithium diisobutylamide and lithium hexamethyleneimide, are soluble in hydrocarbon solvents. Others of the highly substituted lithium amide bases, such as lithium diisopropylamide, are soluble in ether/hydrocarbon solvent mixtures containing less than two equivalents of the ether solvent per mole of the highly substituted lithium amide bases. However, generally, at least two equivalents of the ethereal solvent per mole of highly substituted lithium base should be present in ethereal/hydrocarbon solvent mixtures.

Other useful solvents include highly substituted amine bases (including hexamethyldisilazane, diisopropylamine, hexamethyleneimine, and others as described below) which are employed as a starting reactant in the production of the alkyl metal amides. These bases may be used in excess amounts as solvents in the preparation of their respective highly substituted lithium bases. The use of excess amounts of amine bases can be advantageous to raise reaction temperatures.

The processes of the invention may be generally described as the reaction of an appropriate alkali metal source, such as lithium, potassium, and sodium metal or amides and hydrides thereof, with a substituted amine to provide the corresponding highly substituted alkali metal amide base. The processes of the invention can result in various organic by-products, such as reduced electron carriers and saturated alkanes, and in such instances, further provide for removal of the by-products.

When alkali metal is used, the metal may be employed in the form of powder, sand, shot or larger pieces cut from rods or ingots.

Highly substituted amine bases useful in the production of alkali metal amide bases in accordance with the invention preferably are secondary amines, including, but not limited to, diisopropylamine, hexamethyleneimine, diisobutylamine, tert-butyl-methylamine, tert-butyl-trimethylsilylamine, cyclohexylisopropylamine, cyclohexylmethylamine, allyl-1-phenylethylamine, allyl-1-(R)-1-phenylethylamine, allyl-(S)-1-phenylethylamine, benzyl-1-phenylethylamine, benzyl-(R)-1-phenylethylamine, benzyl-(S)-1-phenylethylamine, bis-(1-phenylethyl)amine, (+)-bis-[(R)-1-phenylethyl]amine, (−)-bis-[(S)-1-phenylethyl]amine, 2,2,6,6-tetramethylpiperidine, pyrrolidine, piperidine and hexamethyldisilazane.

In one embodiment of the invention, an alkali metal source (alkali metal, alkali metal hydride, or alkali metal amide) is reacted with a substituted amine in the absence of an electron carrier to produce an alkali metal amide composition which is substantially free of organic contaminants. When the alkali metal is other than lithium (e.g. potassium or sodium), the alkali metal amide can then be optionally converted into lithium amide by a metathesis reaction with lithium chloride. The resultant insoluble alkali metal chloride can be removed by filtration.

For example, lithium hexamethyldisilazide formulations which are substantially free of organic contaminants can be prepared by any of the following reactions, in a suitable ethereal solvent:

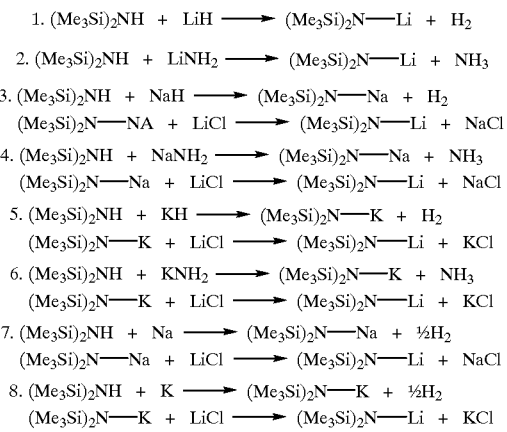

Another embodiment of the present invention comprises reacting an alkali metal with a substituted amine in the presence of an electron carrier in an inert hydrocarbon solvent. Suitable electron carriers generally include conjugated, unsaturated hydrocarbons, such as, but not limited to, styrene, isoprene, butadiene, divinylbenzene, and naphthalene.

The resultant reaction mixture includes alkali metal amide and reduced electron carrier. As the skilled artisan will appreciate, many alkali metal amides are insoluble in hydrocarbons, and thus the resultant amide product will precipitate. Accordingly, this embodiment of the invention is particularly useful for the preparation of alkali metal amides which are insoluble in hydrocarbon solvents. The precipitated alkali metal amide is recovered from the reaction mixture and thereafter washed with an inert hydrocarbon solvent to remove residual reduced electron carrier. The recovered alkali metal amide can then be dissolved in a suitable solvent (i.e., an ethereal solvent) to provide an alkali metal amide composition which is substantially free of organic contaminants. Accordingly, although an electron carrier is used, this process provides for the recovery of the desired product from the reduced carrier.

For example, one equivalent of lithium metal can be reacted with hexamethyldisilazane and one-half an equivalent of an electron carrier (for example, styrene or isoprene) in a hydrocarbon solvent. After the reaction is complete, the reaction mixture is optionally concentrated, and the precipitated lithium hexamethyldisilazide filtered. The resultant filter cake can be washed with a hydrocarbon solvent to remove residual reduced electron carrier. The filter cake is then dried (under an inert atmosphere) and redissolved in an appropriate ethereal or mixed hydrocarbon/ethereal solvent.

Similarly, one equivalent of an alkali metal other than lithium (e.g. potassium or sodium) can be reacted with hexamethyldisilazane and optionally one-half of an equivalent of an electron carrier in a hydrocarbon solvent. Again, after the reaction is complete, the reaction mixture is optionally concentrated, and the precipitated alkali metal hexamethyldisilazide filtered. The filter cake is washed with a hydrocarbon solvent to remove the reduced electron carrier (if present). The filter cake is dried under an inert atmosphere, and then redissolved in the ethereal solvent of choice. The alkali metal hexamethyldisilazide can then be optionally converted into lithium hexamethyldisilazide by a metathesis reaction with lithium chloride. The resultant insoluble alkali metal chloride can be removed by filtration.

In yet another embodiment of the invention, organic contaminant free formulations of alkali metal amides are prepared by reacting an alkali metal with a substituted amine in the presence of an electron carrier in an ethereal, hydrocarbon or mixed ethereal/hydrocarbon solvent. The resultant composition includes alkali metal amide and reduced electron carrier.

To recover the alkali metal amide, the composition is distilled under conditions sufficient to separate the alkali metal amide and the reduced electron carrier. The recovered alkali metal amide can then be suitably treated to provide an alkali metal amide composition which is substantially free of organic contaminants.

For example, organic contaminant free formulations of lithium hexamethyldisilazide can be prepared by reacting one equivalent of lithium metal with hexamethyldisilazane and a half equivalent electron carrier in an ethereal solvent. The reaction mixture is then fed into a continuous rectification unit to remove the reduced electron carrier. The pure solution of lithium hexamethyldisilazide in ethereal solution is thereafter cooled and collected.

This embodiment of the invention is particularly useful when the reduced electron carrier is a low boiling compound (for example, when the electron carrier is isoprene and the reduced electron carrier is 2-methyl-2-butene, which has a boiling point of about 34° C.). In this regard, the reaction mixture which includes the low boiling reduced electron carrier can be distilled under conditions of pressure and temperature sufficient to recover substantially all of the low boiling compound as a component of a low boiling overhead vapor stream without substantial loss of the alkali metal amide in the overhead stream.

However, this aspect of the invention can also be useful for the recovery of alkali metal amides from higher boiling point reduced electron carriers, such as ethylbenzene (from styrene), which has a boiling point of about 136° C. In this regard, distillation conditions are adjusted accordingly.

In yet another embodiment of the invention, high purity organometallic amide compositions can be prepared by reacting an alkali metal with a substituted amine in the presence of an alkyl halide in a hydrocarbon, ethereal, or mixed hydrocarbon/ethereal solvent. The resultant composition includes alkali metal amide and reaction by-products which advantageously are insoluble in the solvent (for example, alkane gases and alkali metal salts). The by-products can then be removed or separated from the composition to provide an alkali metal amide composition which is substantially free of organic contaminants.

For example, amine, solvent, and lithium metal, preferably in bulk form, can be mixed in a stirred reactor. An appropriate alkyl halide, preferably C1 to C4 alkyl halide, and more preferably methyl or ethyl chloride, can be added to the mixture, under optimal conditions for the preparation of the corresponding alkyllithium.

When using methyl or ethyl chloride, the reaction by-products include methane or ethane gas, respectively, which are not soluble in the reaction mixture. The gas can be recovered using conventional venting techniques and thereafter adequately disposed of, for example, by oxidization or burning.

Other by-products include alkali metal salts (for example, lithium chloride), which are typically insoluble in the solvent and thus can be readily separated from the composition using conventional separation techniques, such as filtration.

Alternatively, the alkali metal salt can remain in solution as a complex with the alkali metal amide, depending on the quantity of ethereal solvent used. For example, lithium bis-trialkylsilylamide-LiX complexes are soluble in THF and are more stable than the free amides alone, including a lowered pyrophoricity.

When methyl chloride is used, an appropriate ethereal solvent, such as THF or ethyl ether, can be employed as part of the solvent system to promote the solubility of the resultant alkali metal amide. When ethyl chloride is used, it is possible to employ a solely hydrocarbon solvent medium, and then add the THF after the reaction is completed to dissolve the resultant alkali metal amide. This can vary, depending on the solubility of the resultant amide in the hydrocarbon solvent medium. For example, lithium diisopropylamide and lithium bis-trimethylsilylamide can require added THF for solubility in hydrocarbon media, whereas lithium diisobutylamide and lithium hexamethyleneimide do not.

In still another embodiment of the invention, organometallic amide compositions are prepared in the absence of ethereal solvents. In this aspect of the invention, a substituted amine capable of reacting with an alkali metal to form a hydrocarbon insoluble alkali metal amide is reacted with an alkali metal in an inert hydrocarbon solvent, in the presence of a substituted amine capable of reacting with an alkali metal to form a hydrocarbon soluble alkali metal amide. The resultant reaction mixture includes an insoluble alkali metal amide, which can be recovered from the solution.

The amount of soluble substituted amine precursor present in the reaction mixture can vary from about 5 to about 100 mole percent, based on the insoluble substituted amine precursor. The soluble substituted amine precursor can be recycled and added back into the process. The insoluble alkali metal amide, which separates or precipitates in solution, is recovered or collected from the reaction mixture and dissolved in an appropriate media, i.e., an ether such as THF or an ether/hydrocarbon mixture, to form contaminate free alkali metal amide compositions.

This aspect of the invention is particularly useful for the preparation of compositions which include hydrocarbon insoluble bis-trimethylsilylamides, using hydrocarbon-soluble diisobutylamines and/or hexamethyleneimines.

As described above, various embodiments of the invention can be conducted using ethereal or hydrocarbon solvents, or mixtures thereof. However, as discussed above, excess amine can also be used as the solvent without the presence of other solvents. Still further, excess amine can be used as the solvent, with ethereal solvent (such as THF) being added to the reaction mixture in controlled amounts so as to vary reaction temperatures and/or rates and to insure completion of the reaction when preparing amide products which are insoluble in the amine.

Reaction temperatures for each embodiment of the invention can vary, depending on the nature of the solvent system employed. However, generally each process can be conducted at a temperature below the melting point of lithium, thus imparting economies of manufacture. For example, in THF, reaction temperatures can vary from about 0° C. to the reflux temperature of the reaction mixture (about 68° C. for lithium hexamethyldisilazide). In the presence of an excess amount of amine, the reaction temperature may be as high as 126° C. for this composition. Reaction times can also vary, depending at least in part on reaction temperatures, and can vary from about 1 to about 10 hours.

Typically, in the processes of the invention, the alkali metal source and amine are reacted in stoichiometric amounts, although the reactants can be present in excess amounts.

Although not generally necessary, catalysts may also be used in the present reactions. Preferred catalysts include transition metal salts, such as iron chloride ($FeCl_3$), and other catalysts as described in copending application Ser. No. 08/620,587, filed Mar. 22, 1996.

The following examples further illustrate the invention.

EXAMPLE 1

A distillation apparatus was set-up to include a 500 ml 3-neck flask, 15 plate Oldershaw Vacuum Jacketed Column, reflux splitting head (approximately 10:1 reflux ratio) with condenser, and flasks for receivers, all maintained under an inert atmosphere by an argon back bubbler setup. 214.47 g of a 25.1 weight percent solution of lithium hexamethyldisilazide (LHS) was added to the distillation set-up. The LHS solution was prepared using isoprene as an electron carrier between lithium metal and hexamethyldisilazane (HMDS) in tetrahydrofuran (THF). The solution of LHS was analyzed by gas chromatography (GC) to contain 8.25 GC area % 2-methyl-2-butene.

The golden colored solution was heated with an electric heating mantle for one hour and concentrated by distilling off 16.0 weight percent (34.4 g solvent, boiling point 34–68° C.) which contained mostly 2-methyl-2-butene (bp 36° C.) and THF (bp 67° C.). The resulting golden solution of LHS (180.10 g) was analyzed by GC to contain 0.058 GC area % 2-methyl-2-butene. The solution, by WE titration, contained 29.8 weight percent LHS. Essentially no active LHS was lost during distillation.

The thermal stability of LHS in THF was verified by refluxing (bp 68° C.) for 24 hours. The solution lost only 0.2 percent of LHS as determined by WE titration.

EXAMPLE 2

An oven dried 500 ml three-neck flask, magnetic stirrer, thermocouple, and cold finger condenser were assembled hot with an argon atmosphere using conventional techniques. 9.63 g anhydrous lithium chloride (LiCl) and 65.56 g anhydrous THF were added to the reactor (which was stirred at room temperature for about 2 hours). 42.95 g potassium hexamethyldisilazide (KHS) and two 15 ml rinses with THF (22.52 g) were added. An exotherm from 24.6° C. to 41.8° C. was observed as the KHS dissolved. The resultant tan mixture was next heated to reflux (77° C.). Periodically samples were removed, filtered, and analyzed by ICP for potassium, lithium and chloride. The following was observed:

| Hours at reflux | % Li in solution (LHS) |
| --- | --- |
| 4 | 52.4 |
| 7 | 9.5 |
| 11 | 9.6 |
| 17 | 9.1 |

The foregoing examples are illustrative of the present invention and are not to be construed as limiting thereof. The invention is defined by the following claims, with equivalents of the claims to be included therein.

That which is claimed is:

1. A process for preparing organometallic amide compositions, the process comprising:
   reacting a compound selected from the group consisting of alkali metal hydrides and alkali metal amides with a substituted amine in an ethereal solvent in the absence of an electron carrier to produce an alkali metal amide composition which is substantially free of organic contaminants.

2. The process of claim 1, wherein the ethereal solvent is selected from the group consisting of tetrahydrofuran, 2-methyltetrahydrofuran, diethyl ether, t-butyl methyl ether, dibutyl ether, diethoxymethane, 1,2-dimethoxyethane (glyme), diglyme, triglyme, and mixtures thereof.

3. The process of claim 1, wherein the alkali metal hydride is lithium hydride, sodium hydride or potassium hydride; and the alkali metal amide is lithium amide, sodium amide, or potassium amide.

4. The process of claim 3, wherein the alkali metal hydride is sodium hydride or potassium hydride; and the alkali metal amide is sodium amide or potassium amide; and wherein said process further comprises after said reacting step the step of further reacting the alkali metal amide with a lithium salt to produce a lithium amide.

5. The process of claim 1, wherein the substituted amine is a secondary amine.

6. The process of claim 5, wherein the substituted amine is selected from the group consisting of diisopropylamine, hexamethyleneimine, diisobutylamine, tert-butyl-methylamine, tert-butyl-trimethylsilylamine, cyclohexylisopropylamine, cyclohexylmethylamine, allyl-1-phenylethylamine, allyl-1-(R)-1-phenylethylamine, allyl-(S)-1-phenylethylamine, benzyl-1-phenylethylamine, benzyl-(R)-1-phenylethylamine, benzyl-(S)-1-phenylethylamine, bis-(1-phenylethyl)amine, (+)-bis-[(R)-1-phenylethyl]amine, (−)-bis-[(S)-1-phenylethyl]amine, 2,2,6,6-tetramethylpiperidine, pyrrolidine, piperidine and hexamethyldisilazane.

7. The process of claim 1, wherein the alkali metal amide is lithium diisopropylamide, lithium hexamethyleneimide, lithium diisobutylamide, lithium tert-butyl-methylamide, lithium tert-butyltrimethylsilylamide, lithium cyclohexylisopropylamide, lithium cyclohexylmethylamide, lithium allyl-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(S)-1-phenylethylamide, lithium bis-(1-phenylethyl)amide, lithium (+)-bis-[(R)-1-phenylethyl]amide, lithium (−)-bis-[(S)-1-phenylethyl]amide, lithium 2,2,6,6-tetramethylpiperidide, lithium pyrrolidide, lithium piperidide or lithium hexamethyldisilazide.

8. An organometallic amide composition prepared according to the process of claim 1.

9. A process for preparing organometallic amides, the process comprising:

reacting an alkali metal with a substituted amine in the presence of an electron carrier in an inert hydrocarbon solvent to produce a composition comprising an alkali metal amide and a reduced electron carrier;

recovering the alkali metal amide from the composition; and washing the recovered alkali metal amide with an inert hydrocarbon solvent to remove residual reduced electron carrier.

10. The process of claim 9, further comprising dissolving the recovered alkali metal amide in an ethereal or mixed ethereal/hydrocarbon solvent to provide an alkali metal amide composition which is substantially free of organic contaminants.

11. The process of claim 10, wherein the ethereal solvent is selected from the group consisting of tetrahydrofuran, 2-methyltetrahydrofuran, diethyl ether, t-butyl methyl ether, dibutyl ether, diethoxymethane, 1,2-dimethoxyethane (glyme), diglyme, triglyme, and mixtures thereof.

12. The process of claim 9, wherein the substituted amine is a secondary amine.

13. The process of claim 12, wherein the substituted amine is selected from the group consisting of diisopropylamine, hexamethyleneimine, diisobutylamine, tert-butyl-methylamine, tert-butyl-trimethylsilylamine, cyclohexylisopropylamine, cyclohexylmethylamine, allyl-1-phenylethylamine, allyl-1-(R)-1-phenylethylamine, allyl-(S)-1-phenylethylamine, benzyl-1-phenylethylamine, benzyl-(R)-1-phenylethylamine, benzyl-(S)-1-phenylethylamine, bis-(1-phenylethyl)amine, (+)-bis-[(R)-1-phenylethyl]amine, (−)-bis-[(S)-1-phenylethyl]amine, 2,2,6,6-tetramethylpiperidine, pyrrolidine, piperidine and hexamethyldisilazane.

14. The process of claim 9, wherein the alkali metal is lithium, sodium or potassium.

15. The process of claim 14, wherein:

the alkali metal is sodium or potassium; and said process further comprises after said washing step the step of further reacting the alkali metal amide with a lithium salt to produce a lithium amide.

16. The process of claim 15, wherein:

the lithium salt is a lithium halide;

said further reacting step also produces insoluble sodium or potassium halides; and said process further comprises after said further reacting step the step of separating insoluble sodium or potassium halides from the lithium amide.

17. The process of claim 13, wherein said alkali metal amide is lithium diisopropylamide, lithium hexamethyleneimide, lithium diisobutylamide, lithium tert-butyl-methylamide, lithium tert-butyltrimethylsilylamide, lithium cyclohexylisopropylamide, lithium cyclohexylmethylamide, lithium allyl-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(S)-1-phenylethylamide, lithium bis-(1-phenylethyl)amide, lithium (+)-bis-[(R)-1-phenylethyl]amide, lithium (−)-bis-[(S)-1-phenylethyl]amide, lithium 2,2,6,6-tetramethylpiperidide, lithium pyrrolidide, lithium piperidide or lithium hexamethyldisilazide.

18. An organometallic amide composition prepared according to the process of claim 9.

19. A process for preparing organometallic amide compositions, the process comprising:

reacting an alkali metal with a substituted amine in the presence of an alkyl halide selected from the group consisting of methyl halide, ethyl halide and mixtures thereof in an ethereal, hydrocarbon or ethereal/hydrocarbon solvent system to produce a composition which includes alkali metal amide and reaction by-products which are insoluble in the solvent system; and separating the insoluble reaction by-products from the composition to provide an alkali metal amide composition which is substantially free of organic contaminants.

20. The process of claim 19, wherein the reaction by-products include alkali metal salts and hydrocarbon by-products.

21. The process of claim 19, wherein the solvent system is selected from the group consisting of tetrahydrofuran, 2-methyltetrahydrofuran, diethyl ether, t-butyl methyl ether, dibutyl ether, diethoxymethane, 1,2-dimethoxyethane (glyme), diglyme, triglyme, hexane, cyclohexane, toluene, ethylbenzene, xylene, and mixtures thereof.

22. The process of claim 19, wherein the alkali metal is lithium, sodium or potassium.

23. The process of claim 19, wherein the substituted amine is a secondary amine.

24. The process of claim 23, wherein the substituted amine is selected from the group consisting of diisopropylamine, hexamethyleneimine, diisobutylamine, tert-butyl-methylamine, tert-butyl-trimethylsilylamine, cyclohexylisopropylamine, cyclohexylmethylamine, allyl-1-(R)-1-phenylethylamine, allyl-(S)-1-phenylethylamine, benzyl-1-phenylethylamine, benzyl-(R)-1-phenylethylamine, benzyl-(S)-1-phenylethylamine, bis-(1-phenylethyl)amine, (+)-bis-[(R)-1-phenylethyl]amine, (−)-bis-[(S)-1-phenylethyl]amine, 2,2,6,6-tetramethylpiperidine, pyrrolidine, piperidine and hexamethyldisilazane.

25. The process of claim 19, wherein the alkali metal amide is lithium diisopropylamide, lithium hexamethyleneimide, lithium diisobutylamide, lithium tert-butyl-methylamide, lithium tert-butyltrimethylsilylamide, lithium cyclohexylisopropylamide, lithium cyclohexylmethylamide, lithium ally-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(S)-1-phenylethylamide, lithium bis-(1-phenylethyl)amide, lithium (+)-bis-[(R)-1-phenylethyl]amide, lithium (−)-bis-[(S)-1-phenylethyl]amide, lithium 2,2,6,6-tetramethylpiperidide, lithium pyrrolidide, lithium piperidide or lithium hexamethyldisilazide.

26. An organometallic amide composition prepared according to the process of claim 19.

27. A process for preparing organometallic amide compositions in the absence of ethereal solvents, the process comprising:

reacting a substituted amine capable of reacting with an alkali metal to form a hydrocarbon insoluble alkali metal amide with an alkali metal in an inert hydrocarbon solvent in the presence of a substituted amine capable of reacting with an alkali metal to form a hydrocarbon soluble alkali metal amide to form a reaction mixture that includes an insoluble alkali metal amide;

recovering the insoluble alkali metal amide from the reaction mixture.

28. The process of claim 27, wherein the alkali metal is lithium, sodium or potassium.

29. The process of claim 27, wherein each of the substituted amines is a secondary amine.

30. The process of claim 27, wherein the hydrocarbon soluble amine is diisobutylamine or hexamethyleneimine, and wherein the hydrocarbon insoluble amine is a trialkylsilylamine.

31. The process of claim 27, further comprising after said recovering step the step of treating the recovered insoluble alkali metal amide to provide an alkali metal amide composition.

32. An organometallic amide composition prepared according to the process of claim 27.

33. A process for preparing organometallic amide compositions, the process comprising:
   (a) reacting a compound selected from the group consisting of alkali metal hydrides and alkali metal amides with a substituted amine in the absence of an electron carrier; or
   (b) reacting an alkali metal with a substituted amine in the presence of an electron carrier in an inert hydrocarbon solvent to produce a composition comprising an alkali metal amide and a reduced electron carrier; recovering the alkali metal amide from the composition; and washing the recovered alkali metal amide with an inert hydrocarbon solvent to remove residual reduced electron carrier; or
   (c) reacting an alkali metal with a substituted amine in the presence of an alkyl halide selected from the group consisting of methyl halide, ethyl halide and mixtures thereof in a hydrocarbon, ethereal, or mixed hydrocarbon/ethereal solvent to produce a composition which includes alkali metal amide and insoluble reaction by-products; and separating the reaction by-products from the composition; or
   (d) reacting a substituted amine capable of reacting with an alkali metal to form a hydrocarbon insoluble alkali metal amide with an alkali metal in an inert hydrocarbon solvent in the presence of a substituted amine capable of reacting with an alkali metal to form a hydrocarbon soluble alkali metal amide to form a reaction mixture that includes an insoluble alkali metal amide; and recovering the insoluble alkali metal amide from the reaction mixture.

34. An organometallic amide composition selected from the group consisting of:
   (a) organometallic amide compositions prepared by reacting a compound selected from the group consisting of alkali metal hydrides and alkali metal amides with a substituted amine in the absence of an electron carrier;
   (b) organometallic amide compositions prepared by reacting an alkali metal with a substituted amine in the presence of an electron carrier in an inert hydrocarbon solvent to produce a composition comprising an alkali metal amide and a reduced electron carrier; recovering the alkali metal amide from the composition; and washing the recovered alkali metal amide with an inert hydrocarbon solvent to remove residual reduced electron carrier;
   (c) organometallic amide compositions prepared by reacting an alkali metal with a substituted amine in the presence of an alkyl halide selected from the group consisting of methyl halide, ethyl halide and mixtures thereof in a hydrocarbon, ethereal, or mixed hydrocarbon/ethereal solvent to produce a composition which includes alkali metal amide and insoluble reaction by-products; and separating the insoluble reaction by-products from the composition; and
   (d) organometallic amide compositions prepared by reacting a substituted amine capable of reacting with an alkali metal to form a hydrocarbon insoluble alkali metal amide with an alkali metal in an inert hydrocarbon solvent in the presence of a substituted amine capable of reacting with an alkali metal to form a hydrocarbon soluble alkali metal amide to form a reaction mixture that includes an insoluble alkali metal amide; and recovering the insoluble alkali metal amide from the reaction mixture.

35. A process for preparing organometallic amide compositions, the process comprising:
   reacting a compound selected from the group consisting of alkali metal hydrides and alkali metal amides with a substituted silicon-containing amine in an ethereal solvent in the absence of an electron carrier to produce an alkali metal amide composition of the formula $(R_3M)_xNT(R^1)_y$ wherein M is silicon, R and $R^1$ are C1 to C8 alkyl, cycloalkyl and alkylene groups, x+y=2, and T is an alkali metal, which composition is substantially free of organic contaminants.

36. A process for preparing organometallic amide compositions, the process comprising:
   reacting an alkali metal with a substituted silicon-containing amine in the presence of an electron carrier in an inert hydrocarbon solvent to produce a composition comprising an alkali metal amide of the formula $(R_3M)_xNT(R^1)_y$ wherein M is silicon, R and $R^1$ are C1 to C8 alkyl, cycloalkyl and alkylene groups, x+y=2, and T is an alkali metal, which composition is substantially free of organic contaminants and a reduced electron carrier;
   recovering the alkali metal amide from the composition; and
   washing the recovered alkali metal amide with an inert hydrocarbon solvent to remove residual reduced electron carrier.

37. A process for preparing organometallic amide compositions, the process comprising:
   reacting an alkali metal with a substituted silicon-containing amine in the presence of an alkyl halide selected from the group consisting of methyl halide, ethyl halide and mixtures thereof in an ethereal, hydrocarbon or ethereal/hydrocarbon solvent system to produce a composition which includes alkali metal amide of the formula $(R_3M)_xNT(R^1)_y$ wherein M is silicon, R and $R^1$ are C1 to C8 alkyl, cycloalkyl and alkylene groups, x+y=2, and T is an alkali metal, which composition is substantially free of organic contaminants and reaction by-products which are insoluble in the solvent system; and separating the insoluble reaction by-products from the composition to provide an alkali metal amide composition which is substantially free of organic contaminants.

38. A process for preparing organometallic amide compositions in the absence of ethereal solvents, the process comprising:

reacting a trialkylsilylamine capable of reacting with an alkali metal to form a hydrocarbon insoluble alkali metal amide with an alkali metal in an inert hydrocarbon solvent in the presence of a substituted amine capable of reacting with an alkali metal to form a hydrocarbon soluble alkali metal amide selected from the group consisting of diisobutylamine, hexamethyleneimine, and mixtures thereof, to form a reaction mixture that includes an insoluble alkali metal amide; and recovering the insoluble alkali metal amide from the reaction mixture.

\* \* \* \* \*